(12) United States Patent
Viering

(10) Patent No.: US 9,872,671 B2
(45) Date of Patent: Jan. 23, 2018

(54) CLOSING EUS-FNA NEEDLE

(71) Applicant: Boston Scientific Scimed, Inc., Maple Grove, MN (US)

(72) Inventor: Kirsten Viering, Watertown, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 120 days.

(21) Appl. No.: 14/704,431

(22) Filed: May 5, 2015

(65) Prior Publication Data

US 2015/0320405 A1 Nov. 12, 2015

Related U.S. Application Data

(60) Provisional application No. 61/989,787, filed on May 7, 2014.

(51) Int. Cl.
*A61B 5/00* (2006.01)
*A61B 10/02* (2006.01)

(52) U.S. Cl.
CPC ...... *A61B 10/0266* (2013.01); *A61B 10/0283* (2013.01); *A61B 2010/0208* (2013.01)

(58) Field of Classification Search
CPC . A61B 10/02; A61B 10/0233; A61B 10/0266; A61B 10/0283; A61B 10/06; A61B 2010/0208
See application file for complete search history.

(56) References Cited

U.S. PATENT DOCUMENTS

| 4,682,606 | A | * | 7/1987 | DeCaprio | ......... A61B 10/0266 600/567 |
| 6,416,484 | B1 | * | 7/2002 | Miller | ................. A61B 10/025 600/564 |
| 8,328,738 | B2 | * | 12/2012 | Frankhouser | ........ A61B 10/025 600/587 |
| 8,475,393 | B1 | | 7/2013 | Hameed et al. | |
| 8,728,005 | B2 | * | 5/2014 | McClellan | ......... A61B 10/0266 600/562 |
| 8,894,653 | B2 | * | 11/2014 | Solsberg | ............ A61B 10/0275 606/205 |
| 9,237,884 | B2 | * | 1/2016 | Suzuki | ............... A61B 10/0275 |
| 9,284,948 | B2 | * | 3/2016 | Friedrich | .............. F03D 1/0641 |
| 9,326,754 | B2 | * | 5/2016 | Polster | ............... A61B 10/0266 |

(Continued)

FOREIGN PATENT DOCUMENTS

| WO | 92/10974 | 7/1992 |
| WO | 01/70114 | 9/2001 |

(Continued)

*Primary Examiner* — Max Hindenburg
(74) *Attorney, Agent, or Firm* — Fay Kaplun & Marcin, LLP

(57) ABSTRACT

A needle for fine-needle aspiration includes an elongated body extending from a proximal end to a distal end along a central longitudinal axis and having a channel extending therethrough, a distal portion of the body being movable between a first configuration in which the distal portion extends parallel to the central longitudinal axis and the channel is unobstructed and a second configuration in which the distal portion is axially offset relative to the central longitudinal axis to seal at least a portion of the channel and an actuation mechanism controlling movement of the distal portion between the first and second configurations.

9 Claims, 4 Drawing Sheets

(56) References Cited

U.S. PATENT DOCUMENTS 9,463,001 B2 * 10/2016 Vetter ................ A61B 10/0266
2007/0123890 A1    5/2007 Way et al.
2008/0281226 A1   11/2008 Peters

FOREIGN PATENT DOCUMENTS

| WO | 2006/065913 | 6/2006 |
| WO | 2013/056190 | 4/2013 |
| WO | 2005/086874 | 9/2015 |

* cited by examiner

CLOSING EUS-FNA NEEDLE

PRIORITY CLAIM

The present disclosure claims priority to U.S. Provisional Patent Application Ser. No. 61/989,787 filed May 7, 2014; the disclosure of which is incorporated herewith by reference.

BACKGROUND

Needle biopsies are often performed to diagnose and/or stage pathologies. In these procedures, needles of various size (e.g., 19 gauge, 22 gauge, 25 gauge) may be employed. However, such procedures may be inefficient if the sample of biopsied material is not large enough or is too damaged to perform a target medical diagnostic test or other procedure. In such cases, the needle may need to be repeatedly inserted into the tissue to be sampled until a sample adequate for analysis has been collected. This may increase the costs of and time necessary to complete the procedure while increasing patient discomfort.

SUMMARY OF THE DISCLOSURE

The present disclosure is directed to a needle for fine-needle aspiration, comprising an elongated body extending from a proximal end to a distal end along a central longitudinal axis and having a channel extending therethrough, a distal portion of the body being movable between a first configuration in which the distal portion extends parallel to the central longitudinal axis and the channel is unobstructed and a second configuration in which the distal portion is axially offset relative to the central longitudinal axis to seal at least a portion of the channel and an actuation mechanism controlling movement of the distal portion between the first and second configurations.

In another embodiment, the present disclosure is directed to a needle, wherein the actuation mechanism is a piezoelectric actuator.

In yet another embodiment, the present disclosure is directed to a needle, wherein the actuation mechanism comprises a piezoelectric material attached to at least a portion of a surface of the needle, wherein electric activation of the piezoelectric material moves the distal portion from the first configuration to the second configuration.

In another embodiment, the present disclosure is directed to a needle, wherein the distal portion extends along one side of the needle and is connected to the elongated body via a hinge.

In yet another embodiment, the present disclosure is directed to a needle, wherein the piezoelectric material is attached to a portion of the needle along the hinge.

In another embodiment, the present disclosure is directed to a needle, wherein the hinge is configured to allow movement of the distal portion in only one direction toward the central longitudinal axis.

In yet another embodiment, the present disclosure is directed to a needle, wherein the distal portion is formed as first and second deflectable portions defined by first and second slots extending proximally into the body from the distal end.

In a further embodiment, the present disclosure is directed to a needle, wherein inner surfaces of the first and second deflectable portions include first and second hooks, respectively, extending radially into the channel.

In a still further embodiment, the present disclosure is directed to a needle, wherein the first and second deflectable portions are angled proximally.

In another embodiment, the present disclosure is directed to a needle, wherein the actuation mechanism is one of a piezoelectric actuator, an electro-mechanical actuator and a magnetic actuator.

The present disclosure is also directed to a needle for fine-needle aspiration, comprising an elongated body extending from a proximal end to a distal end along a central longitudinal axis and having a channel extending therethrough, a cutting wire received in a recess extending into an inner surface of the needle, and an actuation mechanism mounted in the channel and movable between a first configuration in which the cutting wire is housed within the recess and a second configuration in which the cutting wire moves out of the recess and into the channel to cut through tissue received in the channel.

In another embodiment, the present disclosure is directed to a needle, wherein a first portion of the recess extends axially relative to the needle from the proximal end to a recess distal end.

In yet another embodiment, the present disclosure is directed to a needle, wherein a second portion of the recess extends circumferentially about the inner surface of the needle at the recess distal end.

In another embodiment, the present disclosure is directed to a needle, wherein the cutting wire is connected to the inner surface of the needle at first and second attachment points located at the second portion of the recess.

In yet another embodiment the present disclosure is directed to a needle, wherein, in the first configuration, the cutting wire extends along a circular path in the second portion of the recess and, in the second configuration, first and second portions of the wire located between the first and second attachment points move toward one another to cut tissue located therebetween.

The present disclosure is also directed to a method for performing a biopsy procedure, comprising inserting a needle to a target location in the body, the needle extending from a proximal end to a distal end and having a channel extending therethrough along a central longitudinal axis, drawing tissue into the channel, and actuating a controller located externally of the body to move an actuatable member located at the distal end of the needle from a first configuration in which the channel is unobstructed and a second configuration in which the actuatable member moves into the channel to cut tissue located adjacent thereto, severing the tissue drawn into the channel from the tissue site.

DETAILED DESCRIPTION

Figure 1:
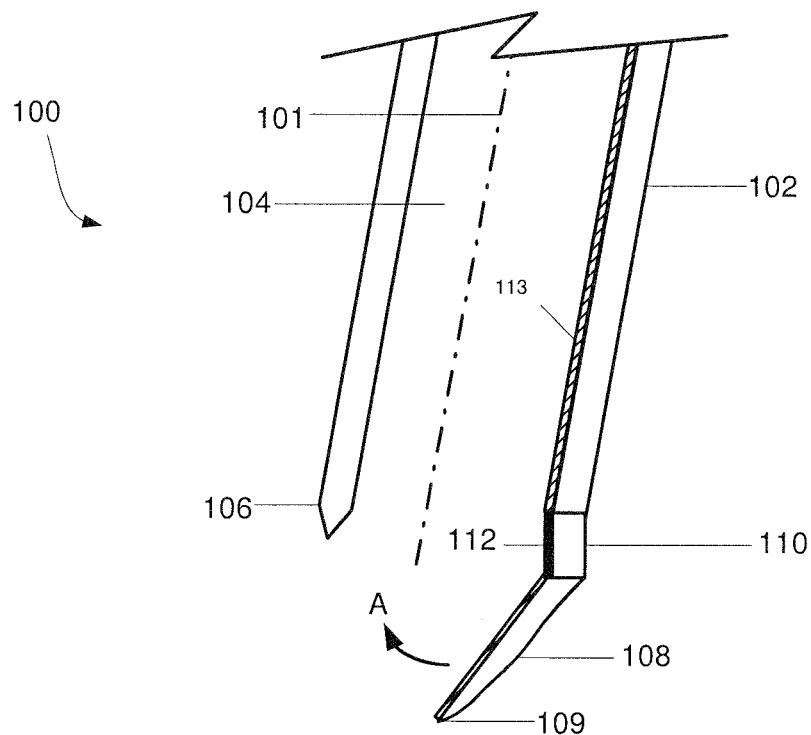
FIG. 1 shows a first cross-sectional view of a device according to a first exemplary embodiment of the present disclosure.

The present disclosure may be further understood with reference to the following description and the appended drawings, wherein like elements are referred to with the same reference numerals. Exemplary embodiments of the present disclosure describe needles for use in fine-needle aspiration ("FNA") procedures. In particular, exemplary embodiments describe actuation mechanisms aiding in severing tissue received in a channel of the needle from a target tissue site as well as mechanisms for retaining captured tissue within the channel until the sample is ready for removal/analysis. A needle according to a first exemplary embodiment includes a distally protruding portion which is movable about a hinged connection. In an operative configuration, the distally protruding portion is actuated to move radially inward to sever tissue adjacent thereto while also closing a distal opening of the needle to retain the captured tissue in the needle. A surface of this needle is attached to a piezoelectric material which, when electrically charged, permits movement of the distally protruding portion from a first configuration in which the distally protruding portion extends parallel to a longitudinal axis of the needle to a second configuration in which the distally protruding portion is offset relative to the longitudinal axis of the needle. It should also be noted that the terms "proximal" and "distal" as used herein are intended to refer to a direction toward (proximal) and away from (distal) a user of the device.

Figure 2:
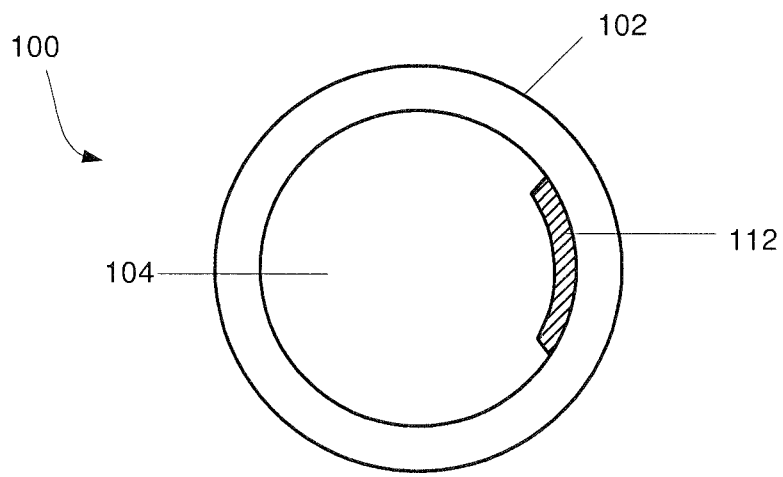
FIG. 2 shows a second cross-sectional view of the device of FIG. 1.

As shown in FIGS. 1-2, a fine-needle aspiration needle 100 according to a first exemplary embodiment comprises an elongated body 102 having a channel 104 extending therethrough. The needle 100 may be a 19-22 gauge needle or another size used in the art. The body 102 extends from a proximal end (not shown) which remains outside the body accessible to a physician or other user to a distal end 106 which is inserted into the body (e.g., through a body lumen accessed via a naturally occurring body orifice). The distal end 106 has a tissue-cutting tip 108. The body 102 according to this embodiment is cylindrical and has substantially uniform outer and inner diameters from the proximal end (not shown) to the distal end 106. The tissue-cutting tip 108 of the needle 100 is coupled to the body 102 by a hinge 110. The hinge 110 permits movement of the tissue-cutting tip 108 relative to the body 102 within a limited predefined range of motion. In a preferred embodiment, the hinge allows movement of the tissue-cutting tip 108 in only one direction, toward the channel 104. In a preferred embodiment, the hinge 110 is movable from a first configuration in which the tissue-cutting tip 108 is axially aligned with the body 102 to a second configuration in which the tissue-cutting tip 108 is bent about the hinge 110 in a direction A. The tissue-cutting tip 108 is bendable from, for example, 0-90° relative to a longitudinal axis 101. In an exemplary embodiment, the tissue-cutting tip 108 is bendable within a range selected so that a distal-most tip 109 thereof does not extend beyond a diameter of the needle 100—i.e., so that the distal-most tip 109 overlies the distal end 106 without extending radially outside an outer edge of the distal end 106 when bent thereacross. Specifically, if a length of the tissue-cutting tip 108 is substantially equivalent to or smaller than a diameter of the needle 100, the tissue-cutting tip 108 may be bent up to 90° relative to the longitudinal axis 101. In another embodiment, where a length of the tissue-cutting tip 108 is selected to be greater than a diameter of the needle 100, the tissue-cutting tip 108 may limited to bend only through an angle smaller than 90° relative to the longitudinal axis 101, the angle being selected so that the tip 109 does not extend radially beyond the outer diameter of the needle 101. This may prevent excess trauma to the patient as the needle 100 is withdrawn after a sample has been obtained. It is noted that the above description is exemplary only and that any combination of length and bendability may be used without deviating from the scope of the disclosure to, for example, conform to the requirements of a particular procedure.

Movement of the tissue-cutting tip 108 about the hinge 110 is controlled by an actuation mechanism such as, for example, a piezoelectric actuator 112 mounted to a portion of the needle 101. In one example, the piezoelectric actuator 112 may be mounted on an inner wall of the needle 101. As shown in greater detail in the cross-sectional view of FIG. 2, the actuator 112 may be formed by a piezoelectric material attached to the inner surface of the needle 101. In one embodiment, the piezoelectric actuator 112 is attached to a predetermined portion of the needle 100 conforming to a position of the tissue-cutting tip 108. In particular, the actuator 112 may be attached to the surface of the needle 101 along the hinge 110 and connected to a proximal portion of the device 100 for delivering energy to the actuator 112 via an electrical connection 113. The piezoelectric actuator 112 may extend about up to 50% of the circumference of the needle 100 although the actuator 112 more preferably extends about 20-25% of the circumference of the needle. Of course, other dimensions for this actuator 112 may be utilized without deviating from the scope of the disclosure. The dimensions of the piezoelectric actuator 112 may be selected so that a piezoelectric force applied by the piezoelectric actuator 112 in an operative configuration is greater than a force require to cut through the target tissue to sever target tissue. A force to bend the needle 101 may be larger than the force to cut the tissue. Although the piezoelectric actuator 112 is shown and described as being attached to an inner surface of the needle 101, the piezoelectric actuator 112 may be attached to any surface of the needle 101 so long as a placement thereof moves the tissue-cutting tip 108 about the hinge 110.

Although the exemplary embodiment describes a piezoelectric actuator 112, the tissue-cutting tip 108 may be moved about the hinge 110 via any of a variety of actuating mechanisms. For example, the tissue-cutting tip 108 may be moved mechanically moved via a controller extending from the tissue-cutting tip 108 to a proximal end of the needle 100.

In accordance with an exemplary method according to the disclosure, the needle 100 is inserted into the body to a target location (e.g., through the working channel of an endoscope or other insertion instrument). In some embodiment, a stylet (not shown) may be positioned within the needle 100 during the insertion process to close the distal opening of the needle 100 preventing unwanted tissue from being lodged in the needle 100. Once the needle has reached the target location, the stylet (not shown) is retracted to open the distal end of the needle 100. The user then inserts the needle 100 into the target tissue (e.g., by manipulating the proximal end of the needle 100) so that target tissue enters the distal end 106 of the needle 100. The piezoelectric actuator 112 is then actuated (e.g., by applying a predetermined electrical voltage thereto (e.g., via conductors embedded in the wall of the needle 100)), to move the tissue-cutting tip 108 from the axially-aligned configuration to the bent configuration in the direction A. As the tissue-cutting tip 108 moves in the direction A, coupled to the tissue received in the needle 100 is severed therefrom, freeing the captured tissue for removal from the body. This freed tissue may be removed from the needle 100 using any means known in the art (e.g., suction, etc.). In another embodiment, the tissue-cutting tip 108 may remain in the closed configuration and the needle 100 may be withdrawn from the body to permit extraction of the tissue sample therefrom with a minimal amount of tissue loss. In some embodiment, needle 100 may be repositioned in the body numerous times to permit the capture of any number of tissue samples without having to remove the needle from the body.

Figure 3:
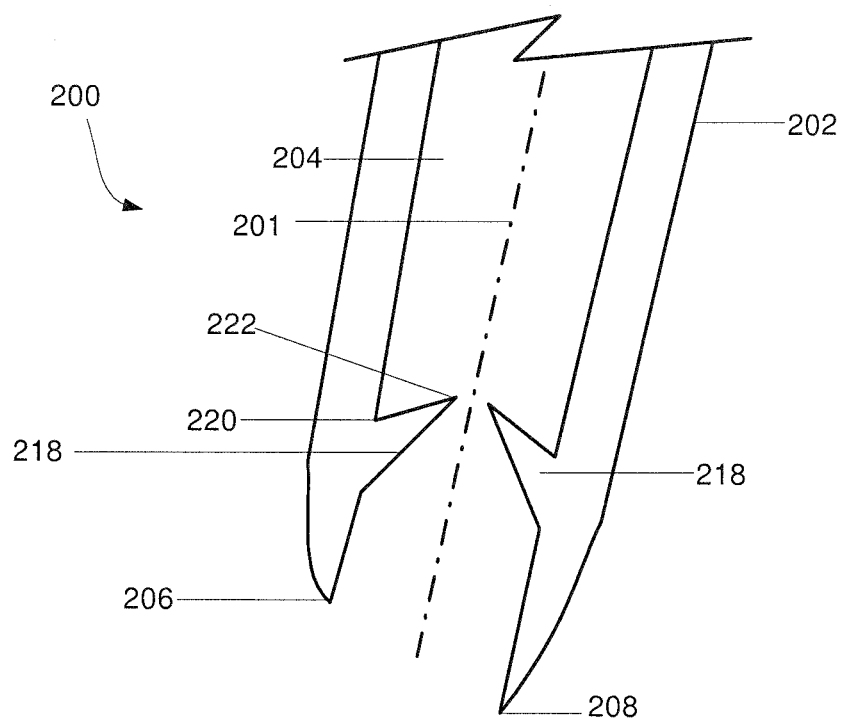
FIG. 3 shows a first cross-sectional view of a device according to a second exemplary embodiment of the present disclosure in a first operative configuration.
Figure 4:
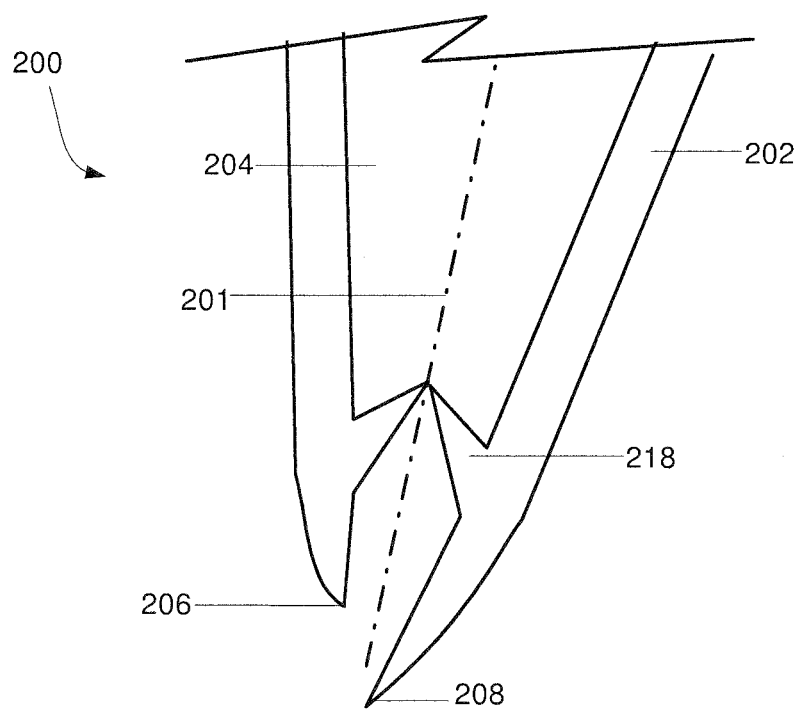
FIG. 4 shows a first cross-sectional view of the device of FIG. 3 in a second operative configuration.
Figure 5:
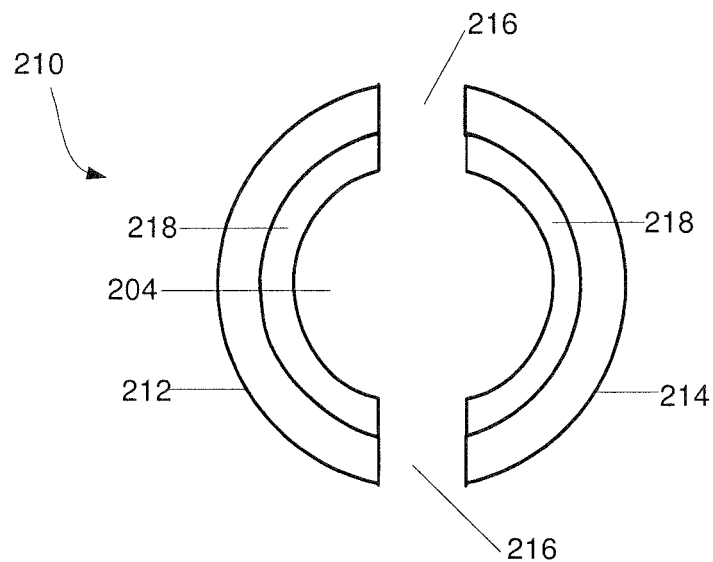
FIG. 5 shows a second cross-sectional view of the device of FIG. 3 in the first operative configuration.
Figure 6:
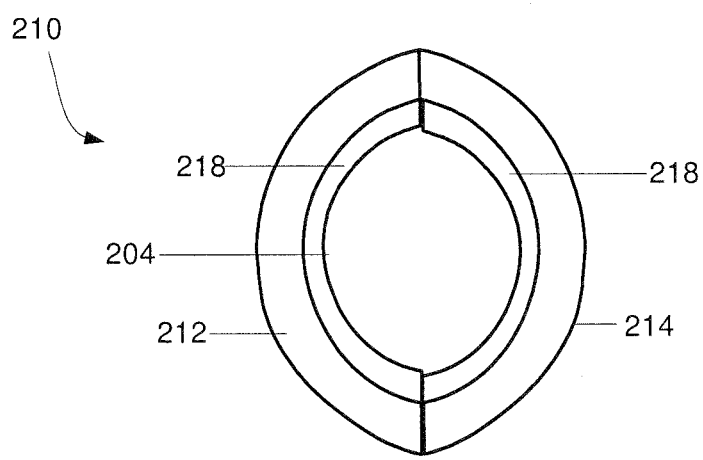
FIG. 6 shows a second cross-sectional view of the device of FIG. 3 in the second operative configuration.

FIGS. 3-6 depict a needle 200 according to another embodiment of the disclosure. The needle 200 includes an elongated body 202 having a channel 204 extending therethrough along a longitudinal axis 201. The needle 200 may be a 19-22 gauge needle or any other size used in the art. The body 202 is cylindrical and, in this embodiment, has a substantially uniform outer and inner diameter from the proximal end (not shown) to a distal end 206 having a tissue-cutting tip 208. The body 202 is separated into a proximal portion (not shown) and a distal portion 210. The proximal portion (not shown) is formed as a unitary cylindrical member. The distal portion includes first and second portions 212, 214 separated from one another by axially extending slots 216. Each of the first and second portions 212, 214 is formed along an arc conforming to the portion of the circular cross-sectional shape of the needle 200, as shown in FIGS. 5 and 6. The slots 216 extend proximally into the body 202 from the distal end 206 a predetermined distance. In one embodiment, the distal portion 210 is coupled to the proximal portion (not shown) by a movable connection (e.g., a hinge). In another embodiment, the proximal and distal portions are integrally formed and defined only by the length of the slots 216. As shown in the top view of FIG. 5, the slots 216 are sized so that, in an open tissue-receiving configuration, first and second portions 212, 214 are separated from one another. As will be described in greater detail later on, the first and second portions 212, 214 are movable to a second, closed configuration in which the gap created by the slots 216 is closed to capture tissue therebetween.

An inner surface of each of the first and second portions 212, 214 includes a hook 218 extending radially inward from a first end 220 coupled to an inner surface of the needle 200 to a second end 222 having a pointed tip. As shown in FIGS. 3-4, the hooks 218 are angled proximally (i.e., so that the second end of each hook 218 is further proximally than is the corresponding first end 220). In a preferred embodiment, each of the hooks 218 extends along an entirety of an inner surface of the one of the first and second portions 212, 214 to which it is attached. In another embodiment, each hook 218 extends about only a portion of the one of the first and second portions 212, 214 to which it is attached. As will be described in greater detail with respect to the exemplary method below, the hooks 218 aid in severing sampled tissue from surrounding tissue and in retaining the severed tissue in place within the needle 200. Although each of the first and second portions 212, 214 are shown as including a single hook 218, the first and second portions 212, 214 may include one or more hook 218, each of the hooks 218 extending about an entirety or a portion of an inner surface of the one of the first and second portions 212, 214 to which it is attached.

The needle 200 may include an actuation mechanism (not shown) moving the first and second portions 212, 214 between the first and second configurations. The actuation mechanism may be one of piezoelectric, electromechanical, mechanical and magnetic. For example, a piezoelectric actuation mechanism may be substantially similar to the actuation mechanism disclosed above with respect to the needle 100, wherein some of the inner surface of the needle 200 is attached to a piezoelectric material which, when actuated, moves the needle 200 from the first configuration to the second configuration. Similarly, the electromechanical and magnetic actuators may include a material deposited over an inner surface of the needle 200 which, when activated by an electrical charge, moves the needle 200 from the first to the second configuration. For example, the material of the electromechanical and magnetic actuators may be the material of the needle itself. Alternatively, a mechanical actuator may be formed by forming the second portion 214 with a bias toward the second configuration. The second portion 214 may be maintained in the first configuration via a stylet when a distal end of the stylet is received between the first and second portions 212, 214 to separate the first and second portions 212, 214. Thus, after a tissue sample has been received within the distal portion 210, the stylet may be withdrawn proximally entirely out of the distal portion 210 freeing the first and second portions 212, 214, respectively, to spring to the second configuration under their natural bias.

In accordance with an exemplary method, the needle 200 is advanced to a target site in the body such that the distal end 206 is located at a target tissue site. After target tissue has been drawn into the needle, an actuator (not shown) is activated (e.g., to apply a predetermined electric charge to the needle). The charge activates a material (e.g., piezoelectric, electromechanical, magnetic, etc.) material deposited on or attached to an inner surface of the first and second portions 212, 214, moving the first and second portions 212, 214 radially inward toward one another. Specifically, the deposited material may be formed such that activation thereof moves the material radially inward toward the central longitudinal axis 201 of the needle 200. As the activated first and second portions 212, 214 move radially inward, the hooks 218 cut through tissue captured in the channel 204 severing it from surrounding tissue. In the second, closed configuration, as shown in FIGS. 4 and 6, the first and second portions 212, 214 are bent radially inward and close off the slots 216, thereby sealing the captured tissue therein. In a preferred embodiment, the needle 200 is maintained in the second, closed configuration until the needle 200 is removed from the body and the sampled tissue can be removed from the channel 204. Multiple passes of the needle 200 are also possible prior to removal of the tissue.

Figure 7:
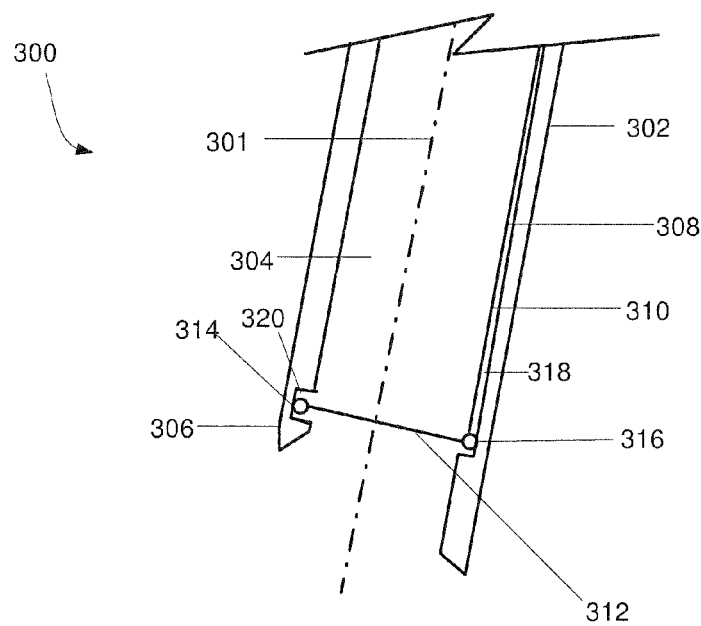
FIG. 7 shows a first cross-sectional view of a device according to a third exemplary embodiment of the present disclosure in a first operative configuration.
Figure 8:
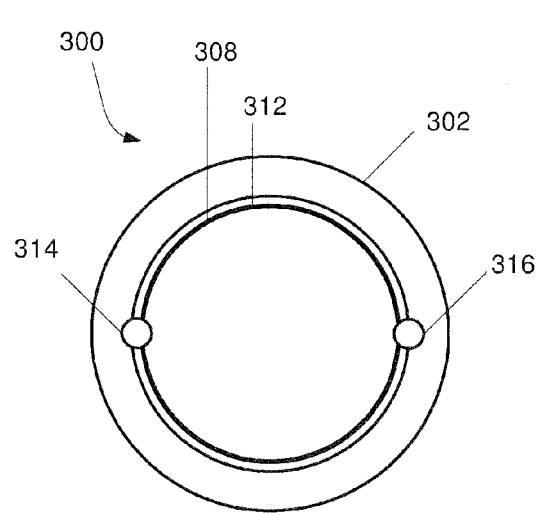
FIG. 8 shows a second cross-sectional view of the device of FIG. 7 in the first operative configuration.
Figure 9:
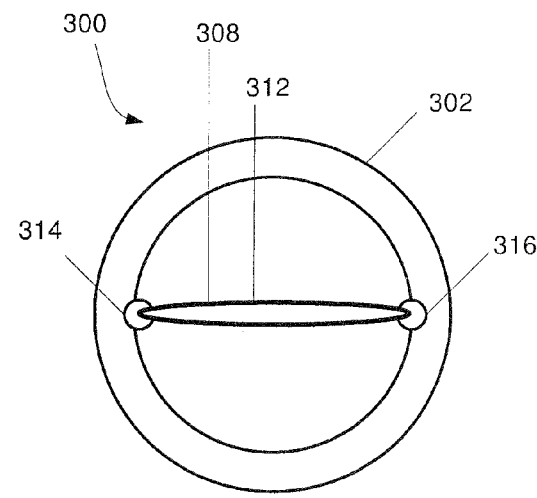
FIG. 9 shows a second cross-sectional view of the device of FIG. 7 in a second operative configuration.

FIGS. 7-9 depict a needle 300 according to another embodiment of the disclosure. The needle 300 includes a body 302 extending from a proximal end (not shown) to a distal end 306 along a longitudinal axis 301 and having a channel 304 extending therethrough. The needle 300 includes a wire-actuation mechanism for severing tissue captured within the channel 304 from surrounding tissue. Specifically, a first portion 310 of a wire 308 extends from a proximal end (not shown of the needle) and along an inner surface thereof parallel to the longitudinal axis. At the distal end 306, the wire extends in a loop 312 about the circumference of the needle 300. Specifically, the wire 308 is connected to the needle at first and second attachment points 314, 316 which may be formed as openings through which the wire 308 is slidably received. An inner surface of the needle 300 may include a first axial recess 318 and a second circumferential recess 320 formed to house the wire 308 therein.

In an operative configuration, the wire 308 is first oriented so that the loop 312 is housed within the circumferential recess 320 to prevent interference with any tissue samples received in the channel 304. Once tissue has been drawn into the channel 304, a proximal end (not shown) of the wire 308 is retracted proximally to constrict the loop 312 about the attachment points 314, 316. As the wire 308 moves from the initial configuration to the tissue-cutting configuration, as shown in FIGS. 8-9, the loop 312 moves to an elliptical shape, cutting any tissue positioned therebetween freeing the tissue received in the channel 304 from the surrounding tissue.

It will be apparent to those skilled in the art that various modifications and variations may be made in the structure and the methodology of the present disclosure, without departing from the scope of the disclosure. Thus, it is intended that the present disclosure cover modifications and variations of the disclosure provided that they come within the scope of the appended claims and their equivalents.

What is claimed is:

1. A needle for fine-needle aspiration, comprising:
   an elongated body extending from a proximal end to a distal end along a central longitudinal axis and having a channel extending therethrough, a distal portion of the body being movable between a first configuration in which the distal portion extends parallel to the central longitudinal axis and the channel is unobstructed and a second configuration in which the distal portion is axially offset relative to the central longitudinal axis to seal at least a portion of the channel, wherein the distal portion extends along one side of the needle for a distance shorter than a diameter of the needle; and
   an actuation mechanism controlling movement of the distal portion between the first and second configurations.

2. The needle of claim 1, wherein the actuation mechanism is a piezoelectric actuator.

3. The needle of claim 2, wherein the actuation mechanism comprises a piezoelectric material attached to at least a portion of a surface of the needle, wherein electric activation of the piezoelectric material moves the distal portion from the first configuration to the second configuration.

4. The needle of claim 3, wherein the distal portion is connected to the elongated body via a hinge.

5. The needle of claim 4, wherein the piezoelectric material is attached to a portion of the needle along the hinge.

6. The needle of claim 4, wherein the hinge is configured to allow movement of the distal portion in only one direction toward the central longitudinal axis.

7. A method for performing a biopsy procedure, comprising:
   inserting a needle to a target location in the body, the needle extending from a proximal end to a distal end and having a channel extending therethrough along a central longitudinal axis;
   drawing tissue into the channel; and
   actuating a controller located externally of the body to move an actuatable member located at the distal end of the needle from a first configuration in which the channel is unobstructed and a second configuration in which the actuatable member moves into the channel to cut tissue located adjacent thereto, severing the tissue drawn into the channel from the tissue site,
   wherein the actuatable member extends along one side of the needle a distance shorter than a diameter of the needle.

8. The method of claim 7, wherein the actuatable member is a deflectable member hingedly connected to the body.

9. The method of claim 7, wherein the actuation mechanism is one of a piezoelectric actuator, an electro-mechanical actuator and a magnetic actuator, the actuation mechanism being electrically activated to charge a material deposited over a surface of the body to cause movement from the first configuration to the second configuration.

* * * * *